US010234376B2

United States Patent
Turick et al.

(10) Patent No.: US 10,234,376 B2
(45) Date of Patent: Mar. 19, 2019

(54) NON-CONTACT MONITORING OF BIOFILMS AND CORROSION ON SUBMERGED SURFACES WITH ELECTROCHEMICAL IMPEDANCE SPECTROSCOPY

(71) Applicant: Savannah River Nuclear Solutions, LLC, Aiken, SC (US)

(72) Inventors: Charles E. Turick, Aiken, SC (US); Charles E. Milliken, Evans, GA (US); Hector Colon-Mercado, Aiken, SC (US); Scott D. Greenway, Aiken, SC (US)

(73) Assignee: SAVANNAH RIVER NUCLEAR SOLUTIONS, LLC, Aiken, SC (US)

( * ) Notice: Subject to any disclaimer, the term of this patent is extended or adjusted under 35 U.S.C. 154(b) by 290 days.

(21) Appl. No.: 14/710,175

(22) Filed: May 12, 2015

(65) Prior Publication Data
US 2016/0334350 A1 Nov. 17, 2016

(51) Int. Cl.
*G01N 17/02* (2006.01)
*G01N 17/04* (2006.01)
*C12Q 1/02* (2006.01)

(52) U.S. Cl.
CPC ............... *G01N 17/04* (2013.01); *C12Q 1/02* (2013.01); *G01N 17/02* (2013.01)

(58) Field of Classification Search
None
See application file for complete search history.

(56) References Cited

U.S. PATENT DOCUMENTS 5,232,596 A 8/1993 Castaldi
6,797,150 B2 9/2004 Kermani et al.
(Continued)

FOREIGN PATENT DOCUMENTS

WO WO2014015187 1/2014

OTHER PUBLICATIONS

Davis et al., "Acoustic and electrical property changes due to microbial growth and biofilm formation in porous media," Journal of Geophysical Research, Vo, 115, Issue G2, Sep. 2010—14 pages.
(Continued)

*Primary Examiner* — Daniel Miller
*Assistant Examiner* — Courtney McDonnough
(74) *Attorney, Agent, or Firm* — Dority & Manning, P.A.

(57) ABSTRACT

Systems and methods for monitoring microorganisms on a surface are provided. In particular, a flat, patterned sensing electrode can be positioned proximate a surface in non-contact relationship with the surface. The sensing electrode can include a working electrode and a counter electrode. The surface and the sensing electrode can be submerged in an aqueous medium. An alternating current signal can be applied at the working electrode. The signal can propagate through the aqueous medium and can be measured at the counter electrode. The presence of microorganisms on the surface can cause changes in the signal as the signal propagates through the aqueous medium. Such changes in the signal can be used to determine impedance parameters, which can correspond to microbial characteristics associated with the surface. For instance, the microbial characteristics can be associated with a biofilm, corrosion and/or biocorrosion on the surface.

20 Claims, 5 Drawing Sheets

(56) References Cited

U.S. PATENT DOCUMENTS

| | | | |
|---|---|---|---|
| 6,885,960 B2 | 4/2005 | Wagner et al. | |
| 7,022,212 B2 | 4/2006 | Zdunek | |
| 7,022,287 B2 | 4/2006 | Schoeniger et al. | |
| 7,043,402 B2 | 5/2006 | Phillips et al. | |
| 7,147,779 B1 | 12/2006 | Phifer et al. | |
| 7,238,496 B2 | 7/2007 | Li et al. | |
| 7,444,856 B2 | 11/2008 | Prinz et al. | |
| 7,666,285 B1* | 2/2010 | Cho | B01L 3/502715 137/814 |
| 7,880,484 B2 | 2/2011 | Miller et al. | |
| 8,052,873 B1 | 11/2011 | Foster et al. | |
| 8,072,711 B1 | 12/2011 | Wang | |
| 8,084,274 B2 | 12/2011 | Seul et al. | |
| 8,310,243 B2 | 11/2012 | Shukla et al. | |
| 8,416,417 B2 | 4/2013 | Foley et al. | |
| 8,766,641 B2 | 7/2014 | Pindiprolu et al. | |
| 2003/0052059 A1 | 3/2003 | Boyette et al. | |
| 2003/0116447 A1 | 6/2003 | Surridge et al. | |
| 2004/0012399 A1 | 1/2004 | Lin et al. | |
| 2006/0088945 A1* | 4/2006 | Douglas | C12Q 1/001 436/518 |
| 2009/0273356 A1 | 11/2009 | Pampin et al. | |
| 2011/0035157 A1 | 2/2011 | Berbel et al. | |
| 2011/0100820 A1 | 5/2011 | Bachmann et al. | |
| 2011/0144469 A1 | 6/2011 | Connolly et al. | |
| 2011/0298481 A1* | 12/2011 | Mayer | G01N 27/227 324/686 |
| 2012/0070338 A1 | 3/2012 | Schaeffer et al. | |
| 2012/0200302 A1 | 8/2012 | Wang | |
| 2014/0326340 A1* | 11/2014 | Kuriki | C23F 11/18 422/82.02 |

OTHER PUBLICATIONS

Shimizu et al., "Electrochemical Impedance Study of the Hematite/Water Interface," Langmuir, vol. 28, pp. 7914-7920, Apr. 27, 2012.

Wu et al., "Calcite precipitation dominates the electrical signatures of zero valent iron columns under simulated field conditions," Journal of Geophysical Research, vol. 115, Issure G2, Jun. 2010—10 pages.

Aal et al., "Effect of bioclogging in porous media on complex conductivity signates," Journal of Geophysical Research, vol. 115, Issue G3, Sep. 2010—10 pages.

Aal et al., "Sensitivity of geoelectrical measurements to the presence of bacteria in porous media," Journal of Geophysical Research, vol. 11, Issue G3, Sep. 2010—11 pages.

* cited by examiner

NON-CONTACT MONITORING OF BIOFILMS AND CORROSION ON SUBMERGED SURFACES WITH ELECTROCHEMICAL IMPEDANCE SPECTROSCOPY

GOVERNMENT SUPPORT CLAUSE

This invention was made with Government support under Contract No. DE-AC09-08SR22470, awarded by the U.S. Department of Energy. The Government has certain rights in the invention.

FIELD

The present disclosure relates generally to monitoring biofilms, bio-corrosion, and/or corrosion on surfaces, such as submerged surfaces.

BACKGROUND

The monitoring of biofilms and corrosion on surfaces can be important for many applications, including bioremediation, waste containment, and other applications. In particular applications, it can be important to monitor characteristics (e.g. growth) of biofilm, bio-corrosion, and/or corrosion on a submerged surface, such as the surface of an underground storage tank, pipeline, or concrete containment structure. Monitoring the presence of a biofilm, bio-corrosion, and/or corrosion on submerged surfaces can be particularly useful in identifying possible contamination events leading to or resulting from, for instance, spills, leaks, and other contamination events.

Electrochemical impedance spectroscopy (EIS) is a technique that can be used to monitor various parameters of electrochemical systems through monitoring of impedance parameters. EIS systems can include a working electrode and a counter electrode. The EIS system can evaluate the impedance of a surface by applying an AC signal with variable frequency through the pair of electrodes while measuring the resulting current. The real and imaginary parts of the impedance can be plotted as a function of frequency and analyzed to extract parameters of the system. EIS systems have been used to monitor the growth and other characteristics of biofilms. Such systems, however, have typically monitored growth of the biofilm on one of the working electrode or counter electrode.

SUMMARY

Aspects and advantages of embodiments of the present disclosure will be set forth in part in the following description, or may be learned from the description, or may be learned through practice of the embodiments.

One example aspect of the present disclosure is directed to a system for monitoring microorganisms on a surface. The system includes a flat, patterned electrode having a working electrode and a counter electrode. The flat, patterned electrode is positioned proximate the surface in non-contact relationship with the surface. The system further includes a signal source coupled to the flat, patterned electrode. The signal source is configured to apply an alternating current signal to the working electrode at one or more frequencies. The system further includes a processing device configured to detect a measured signal at the counter electrode. One or more characteristics of the measured signal at the counter electrode are indicative of one or more characteristics of microorganisms on the surface.

Other example aspects of the present disclosure are directed to systems, methods, apparatus, tangible, non-transitory computer-readable media, user interfaces, memory devices, and electronic devices for monitoring microorganisms on a surface.

These and other features, aspects and advantages of various embodiments will become better understood with reference to the following description and appended claims. The accompanying drawings, which are incorporated in and constitute a part of this specification, illustrate embodiments of the present disclosure and, together with the description, serve to explain the related principles.

BRIEF DESCRIPTION OF THE DRAWINGS

Detailed discussion of embodiments directed to one of ordinary skill in the art are set forth in the specification, which makes reference to the appended figures, in which.

DETAILED DESCRIPTION

Reference now will be made in detail to embodiments, one or more examples of which are illustrated in the drawings. Each example is provided by way of explanation of the embodiments, not limitation of the present disclosure. In fact, it will be apparent to those skilled in the art that various modifications and variations can be made to the embodiments without departing from the scope or spirit of the present disclosure. For instance, features illustrated or described as part of one embodiment can be used with another embodiment to yield a still further embodiment. Thus, it is intended that aspects of the present disclosure cover such modifications and variations.

Example aspects of the present disclosure are directed to monitoring microorganisms on a surface. For instance, a sensing electrode can be placed proximate a surface to identify microbial activity associated with the surface. The sensing electrode can be a flat, patterned electrode having a working electrode and a counter electrode. The sensing electrode can be used to implement electrochemical impedance spectroscopy (EIS) on the surface. As indicated above, EIS can be used to identify impedance parameters associated with the surface.

In example embodiments, the monitored surface can be submerged in an aqueous medium. The sensing electrode can be placed in the aqueous medium proximate the surface in non-contact relationship with the surface. As used herein, a non-contact relationship can be a positional relationship between two or more objects or entities, such that none of the two or more objects or entities make physical contact with any other of the two or more objects or entities. For instance, the sensing electrode can be placed in the aqueous medium a range of about 0.1 millimeters to about 100 centimeters above the surface. As used herein, the term "about," when used in reference to a numerical value, is intended to refer to within 20% of the numerical value.

In this manner, the surface is not disturbed by the sensing electrode. As indicated above, an alternating current (AC) signal can be applied to the working electrode. In particular, the signal can be an AC potential applied at the working electrode over a range of frequencies. In example embodiments, microorganisms located on the surface can cause the signal to change as the signal propagates through the aqueous medium. The signal can then be measured at the counter electrode. In particular, an AC current can be measured at the counter electrode. The applied potential and the measured current can then be used to determine impedance parameters associated with the surface.

Such impedance parameters can be derived at least in part from changes in the applied signal due to the presence of microorganisms on the surface. For instance, such changes can include changes in the current, phase, and/or amplitude of the signal. Such changes can vary over the range of frequencies. The identified impedance parameters can include absolute impedance, real (e.g. in-phase) impedance, and/or imaginary (out-of-phase) impedance associated with the signal. Such impedance parameters can be used to further determine a conductivity (e.g. real and/or imaginary conductivity) associated with the surface.

The various signal parameters can provide information relating to various microbial activity in the surface caused, for instance, by the presence of a biofilm, corrosion, and/or bio-corrosion on the surface. Such information can be useful regarding microbial cultures. In particular, impedance parameters associated with the surface can change as the microbial cultures on the surface convert carbon sources to waste products. Such changes can be used to identify microbial activity. In example embodiments, absolute impedance can be plotted against frequency (e.g. Bode plot) to determine general information associated with impedance and admittance. Further, imaginary impedance can be plotted against real impedance (e.g. Nyquist plot) to determine information indicative of reaction rates and diffusion phenomena. As another example, phase shift of the measured current relative to the applied potential can correspond to geochemical transformations at low frequencies (e.g. about 0.01 Hz to about 1.0 Hz). Further, at mid-level frequencies (e.g. about 10 Hz to about 1000 Hz), phase shift can correspond to microbial density.

Information relating to microbial growth can also be determined from the impedance parameters. For instance, imaginary conductivity can correspond to the ability to store energy and/or lipid membrane signatures. Real relative permittivity can also be used to measure microbial activity and/or growth. For instance, real relative permittivity can correspond to cell membrane charge, and can indicate cell viability.

Figure 1:
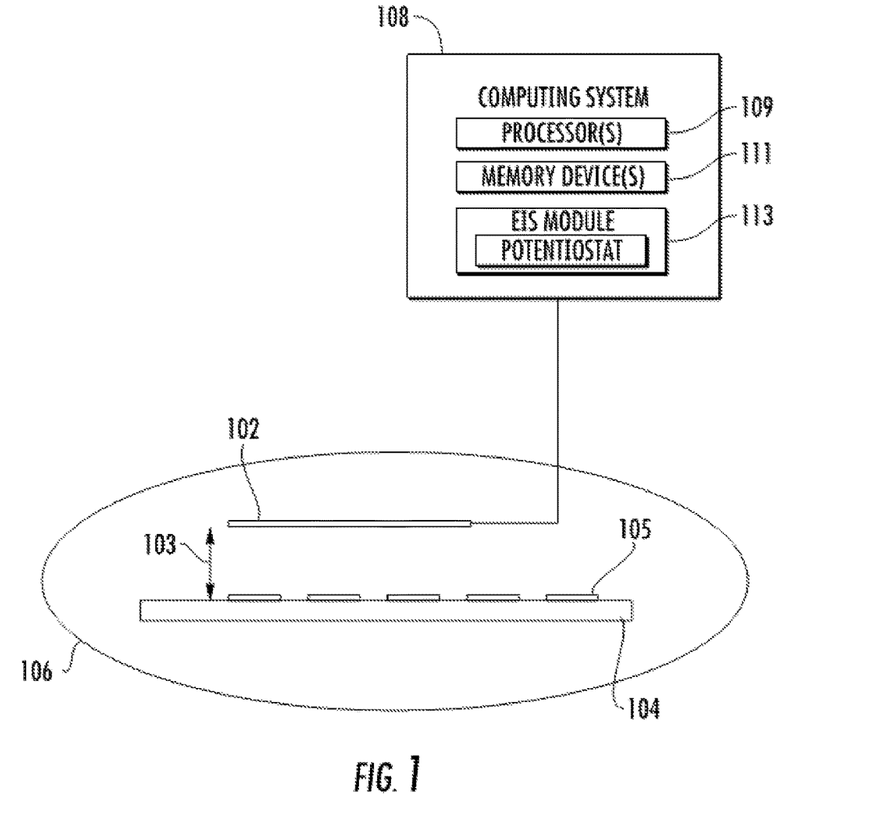
FIG. 1 depicts an example system for monitoring microorganisms on a surface according to example embodiments of the present disclosure.

Referring now to the figures, FIG. 1 depicts an example system 100 for monitoring microorganisms on a surface according to example embodiments of the present disclosure. System 100 includes a sensing electrode 102 and a surface 104. Sensing electrode 102 and surface 104 can both be submerged in an aqueous medium 106. Various microorganisms 105 can be attached to surface 104. Such microorganisms 105 can form a biofilm, and/or cause bio-corrosion on the surface. Sensing electrode 102 can include a working electrode and a counter electrode, and can be used to monitor the microbial activity on the surface through electrochemical impedance spectroscopy (EIS). As indicated above, sensing electrode 102 can be positioned proximate surface 104. As depicted in FIG. 1, sensing electrode 102 can be placed a distance 103 from surface 104. In example embodiments, distance 103 can be a distance in a range of about 0.1 millimeters to about 100 centimeters from surface 104. For instance, distance 103 can be a range of about 1 millimeter to about 4 millimeters, a range of about 1.5 millimeters to about 3.5 millimeters, or a range of about 3 millimeters from surface 104.

Sensing electrode 102 can implement EIS to determine impedance parameters associated with surface 104. The impedance parameters can be determined, for instance, by a computing system 108 coupled to sensing electrode 102 based on signals detected at sensing electrode 102.

Computing system 108 can be any suitable type of computing device, such as a general purpose computer, special purpose computer, laptop, desktop, mobile device, smartphone, tablet, wearable computing device, a display with one or more processors, or other suitable computing device. Computing system 108 can include one or more processor(s) 109 and one or more memory device(s) 111.

The one or more processor(s) 109 can include any suitable processing device, such as a microprocessor, microcontroller, integrated circuit, logic device, one or more central processing units (CPUs), graphics processing units (GPUs) dedicated to efficiently rendering images or performing other specialized calculations, and/or other processing devices. The one or more memory device(s) 111 can include one or more computer-readable media, including, but not limited to, non-transitory computer-readable media, RAM, ROM, hard drives, flash memory, or other memory devices.

The one or more memory device(s) 111 store information accessible by the one or more processor(s) 109, including instructions that can be executed by the one or more processors. For instance, the memory devices can store instructions for monitoring microorganisms on a surface according to example embodiments of the present disclosure.

Computing system 108 can further include an EIS module 113. EIS module 113 can be used to determine impedance parameters associated with surface 104. EIS module can include a potentiostat used to provide a signal to sensing electrode 102 and detect a measured signal at sensing electrode 102.

As used herein, the term "module" can be defined as computer logic used to provide desired functionality. As such, a module can be implemented in various manners. For instance, a module can be implemented in hardware devices, application specific circuits, firmware and/or software used to control one or more general purpose processors. In example embodiments, modules can be program code files that are stored on a storage device, loaded into memory and executed by a processor. In alternative embodiments, modules can be provided from computer program products (e.g. computer executable instructions) that are stored in a tangible computer-readable storage medium such as RAM, a hard disk or optical or magnetic media.

According to example embodiments of the present disclosure, an AC potential can be applied at the working electrode of sensing electrode 102. The signal can propagate through the aqueous medium and the microorganisms, and can then be received by the counter electrode. An AC current can then be measured at the counter electrode, and data indicative of the measured current can then be received by computing system 108. Computing system 108 can then determine impedance parameters associated with surface 104 based at least in part on the measured current and the applied potential. As described above, the impedance parameters can correspond to characteristics of microorganisms on surface 104.

Figure 2:
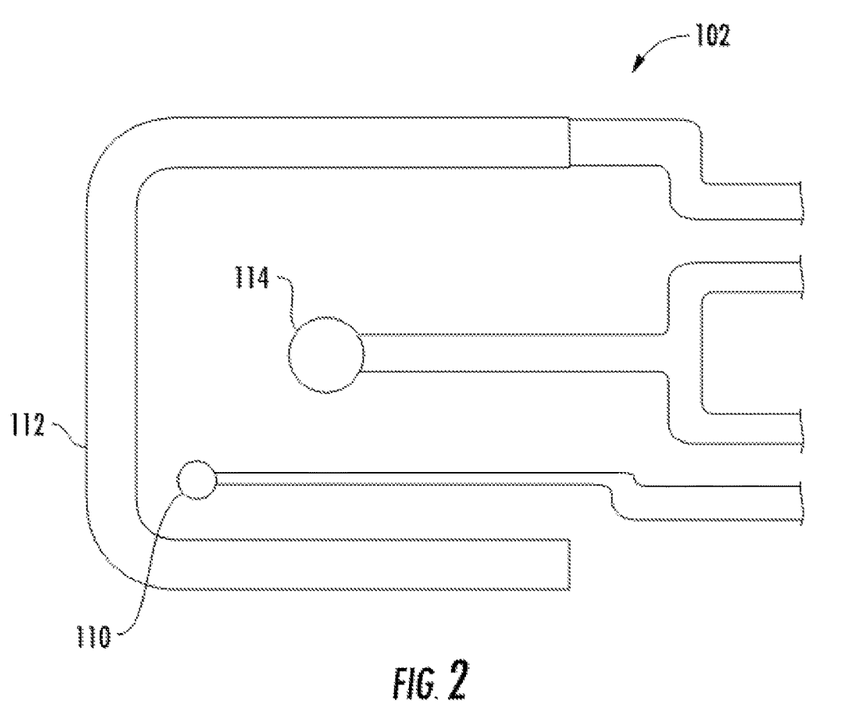
FIG. 2 depicts an example sensing electrode according to example embodiments of the present disclosure.

FIG. 2 depicts an example sensing electrode 102 according to example embodiments of the present disclosure. Although FIG. 2 depicts a three-electrode cell, it will be appreciated that various other electrode configurations can be used, such as a two electrode cell or a four electrode cell. Sensing electrode 102 can include a reference electrode 110, a counter electrode 112 and a working electrode 114. During EIS, reference electrode 110 can have a constant (or near constant), known reference potential. In this manner, a potential applied at working electrode 114 can be measured relative to the reference potential. The signal applied at working electrode 114 can propagate through a medium and can be received by counter electrode 112. According to example embodiments of the present disclosure, when sensing electrode 102 is positioned in an aqueous medium proximate a surface, such as surface 104, the aqueous medium and microorganisms located on the surface can cause alterations in the signal. As indicated above, the changes in the signal can correspond to impedance parameters associated with the surface can correspond to various microbial characteristics of the surface.

In alternative embodiments, sensing electrode 102 can be used to implement various other electrochemical techniques such as voltammetry. For instance, linear sweep voltammetry and/or cyclic voltammetry can be implemented using sensing electrode 102. In linear sweep voltammetry, the AC potential applied at the working electrode is increased linearly over time. In cyclic voltammetry, the AC potential applied at the working electrode is cycled over time. According to example embodiments of the present disclosure, linear sweep voltammetry and cyclical voltammetry can be used to more fully interrogate the surface for such features as contaminant concentrations and/or electron shuttles, with some potential to detect unknown or unexpected contaminants.

Sensing electrode 102 can be made from various suitable materials. For instance, sensing electrode 102 can include a ceramic substrate. Working electrode 114 and counter electrode 112 can be gold or platinum electrodes. Reference electrode 110 can be a silver and/or silver chloride electrode. It will be appreciated by those skilled in the art that various other suitable materials can be used. In addition, it will be appreciated that sensing electrode 102 can be any suitable size.

Figure 3:
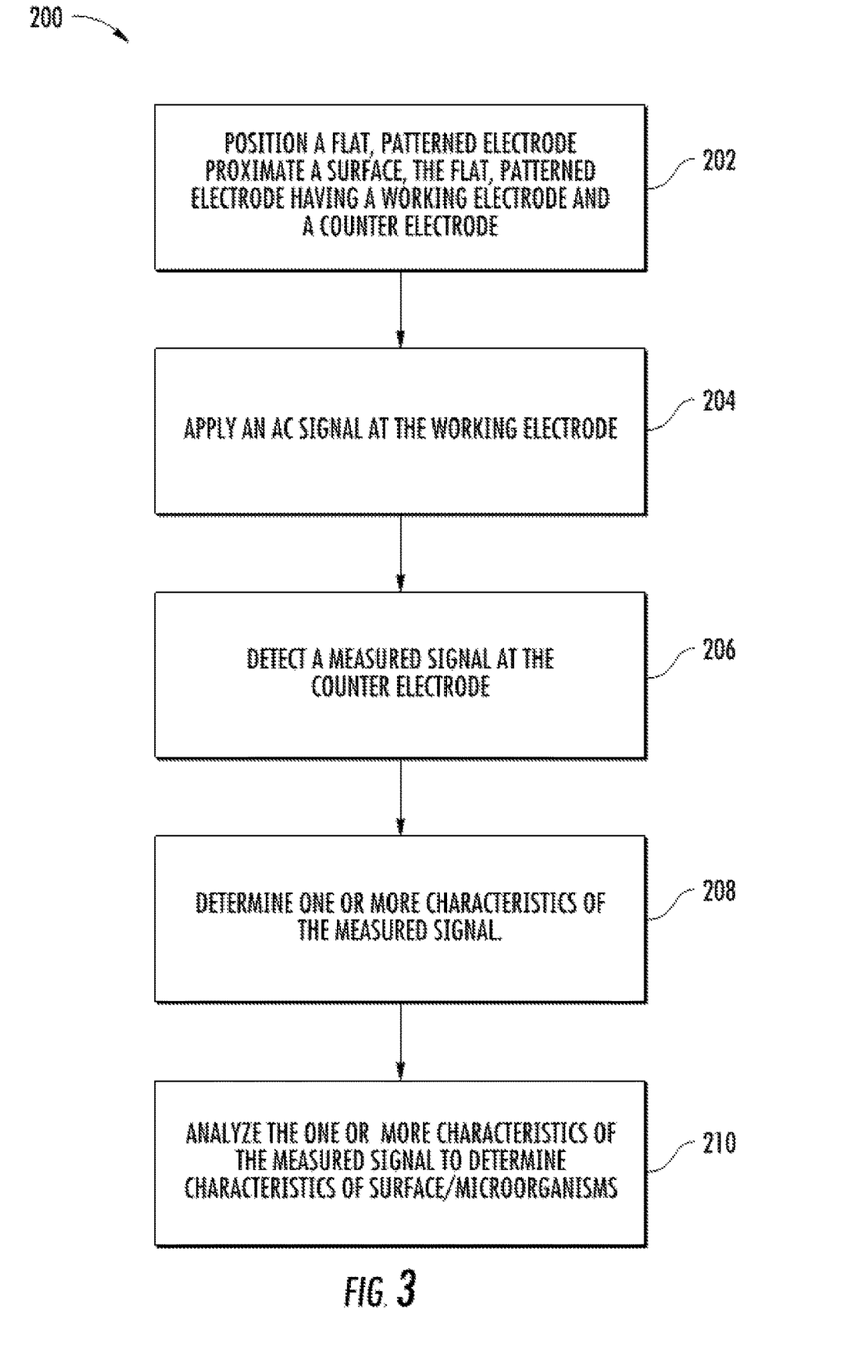
FIG. 3 depicts a flow diagram of an example method of monitoring microorganisms on a surface according to example embodiments of the present disclosure.

FIG. 3 depicts a flow diagram of an example method (200) of monitoring microorganisms on a surface according to example embodiments of the present disclosure. FIG. 3 can be implemented using a sensing electrode, such as sensing electrode 102 of FIG. 2, and one or more computing devices, such as computing system 108 of FIG. 1. In addition, FIG. 3 depicts steps performed in a particular order for purposes of illustration and discussion. Those of ordinary skill in the art, using the disclosures provided herein, will understand that the steps of any of the methods disclosed herein can be adapted, omitted, rearranged, expanded, or modified in various ways without deviating from the scope of the present disclosure.

At (202), method (200) can include positioning a flat, patterned electrode proximate a surface. The flat, patterned electrode can have a working electrode and a counter electrode, and can be used to implement EIS and/or various other electrochemical techniques on the surface. The flat, patterned electrode can be in non-contact relationship with the surface. In example embodiments, the surface can be submerged in an aqueous medium and the flat, patterned electrode can be positioned in the aqueous medium a range of about 0.1 millimeters to about 100 centimeters from the surface.

At (204), method (200) can include applying an AC signal at the working electrode. For instance, the applied signal can be an AC potential. At (206), method (200) can include detecting a measured signal at the counter electrode. For instance, the measured signal can be a current signal. As indicated above, as the applied AC signal propagates through the aqueous medium, the presence of microorganisms (e.g. a biofilm) on the surface can cause alterations in the signal.

At (208), method (200) can include determining one or more characteristics of the measured signal. For instance, the one or more characteristics of the measured signal can include a phase change of the signal relative to the applied signal, and/or various impedance parameters associated with the surface and the aqueous medium (e.g. imaginary impedance, real impedance, absolute impedance, conductivity, relative permittivity, etc.). Impedance is a measurement of resistance in the presence of an AC potential. Impedance can be determined by applying an AC potential and measuring the current through a cell. In complex systems, an impedance value ($Z$) can include a real (e.g. in-phase) impedance ($Z'$) and an imaginary (e.g. out-of-phase) impedance ($Z''$). Imaginary impedance can be derived from a phase shift of the current relative to the AC potential. The real and imaginary impedances can be used to derive an absolute (e.g. absolute magnitude) impedance value ($|Z|$). In particular, absolute impedance can be determined at least in part from the degree to which a medium changes the amplitude and/or phase of a signal propagating through the medium.

At (210), method (200) can include analyzing the one or more characteristics of the measured signal to determine characteristics of microorganisms located on the surface. As described above, such characteristics of microorganisms can be related to a biofilm on the surface, corrosion on the surface, and/or bio-corrosion on the surface. In particular, the characteristics of microorganisms can include microbial activity, microbial growth, mineralogy, reaction rates, biogeochemical changes, energy storage, polarization, cell viability etc.

Figure 4:
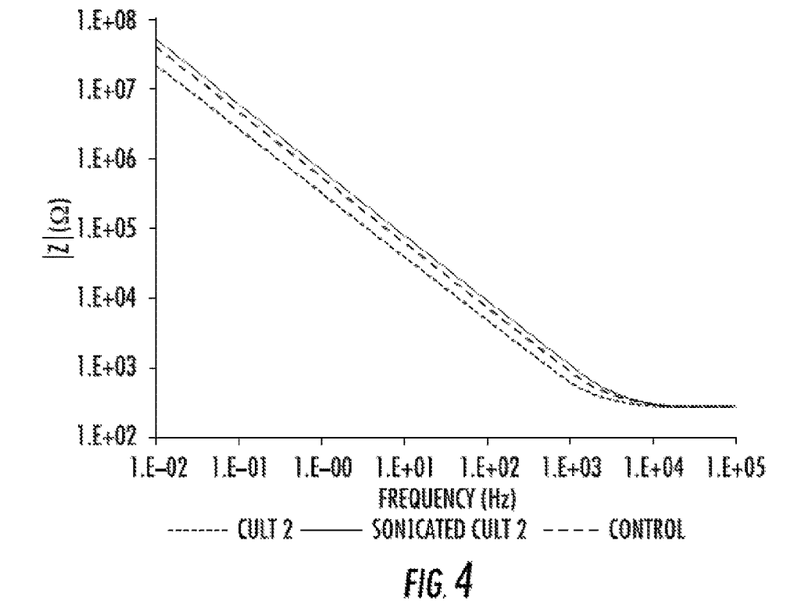
FIG. 4 depicts a diagram of absolute impedance of a surface over a range of frequencies according to example embodiments of the present disclosure.

According to example embodiments of the present disclosure, the impedance parameters associated with the submerged surface can change as microbial characteristics of the surface change. In particular, microorganisms on the surface can cause alterations in a signal propagating through the aqueous medium (e.g. a change in phase and/or amplitude of the signal), which can cause a change in impedance. For instance, FIG. 4 depicts absolute impedance associated with various surfaces over a range of frequencies. In FIG. 4, Cult 2 represents an aluminum coupon with an attached biofilm having high biomass concentrations, Sonicated Cult 2 represents an aluminum coupon after having a biofilm removed through sonication, and Control represents a sterile aluminum coupon. As depicted, Cult 2 demonstrates differences in absolute impedance when compared to Sonicated Cult 2 and Control. Such differences in absolute impedance can be used to measure changes in microbial characteristics of the aluminum coupons.

Figure 5:
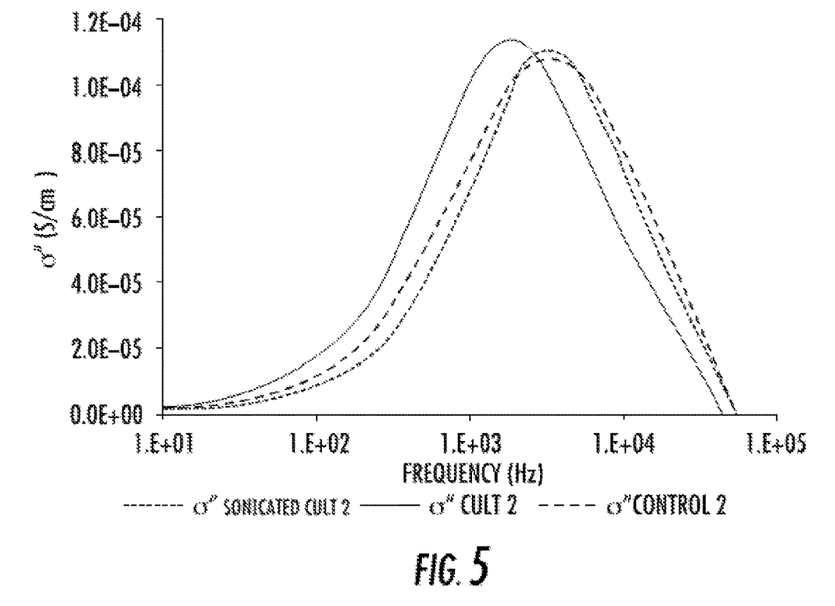
FIG. 5 depicts a diagram of imaginary conductivity of a surface over a range of frequencies according to example embodiments of the present disclosure.

Impedance can be further used to determine conductivity associated with the surface. Impedance is the inverse of admittance, which corresponds to conductivity in complex systems. Accordingly, the conductivity of a surface can also change as the microbial characteristics of the surface change. For instance, FIG. 5 depicts imaginary conductivity associated with various surfaces over a range of frequencies. In FIG. 5, like in FIG. 3, Cult 2 represents an aluminum coupon with an attached biofilm having high biomass concentrations, Sonicated Cult 2 represents an aluminum coupon after having a biofilm removed through sonication, and Control represents a sterile aluminum coupon. As depicted, Cult 2 demonstrates differences in imaginary conductivity when compared to Sonicated Cult 2 and Control. Such differences in imaginary conductivity can be used to measure changes in microbial characteristics of the aluminum coupons. In particular, changes in imaginary conductivity can correspond to energy storage and/or polarization related to cells and cellular activity on a surface.

Figure 6:
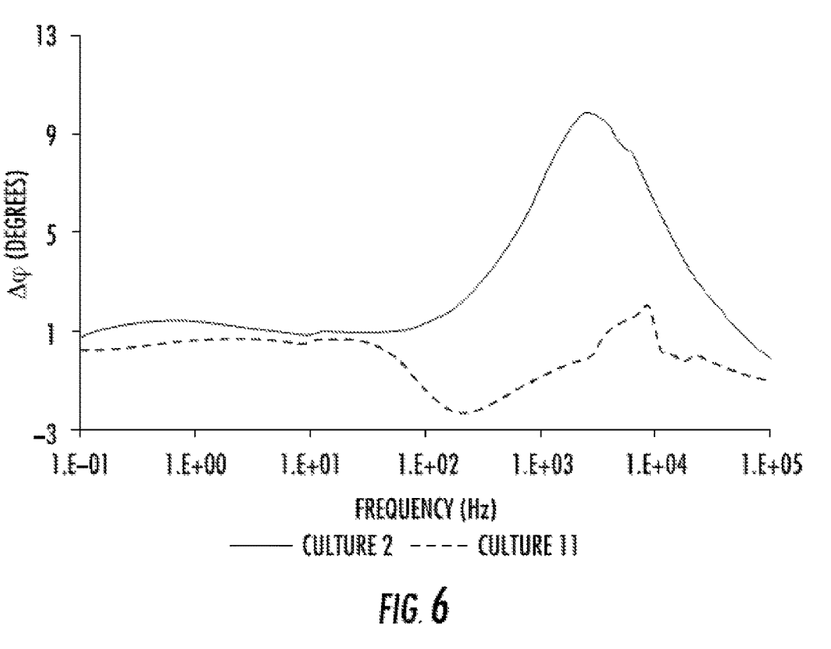
FIG. 6 depicts a diagram of phase shift of a signal over a range of frequencies according to example embodiments of the present disclosure.

In example embodiments, the phase shift of the measured AC signal relative to the applied AC potential can also correspond to microbial characteristics associated with a surface. For instance, FIG. 6 depicts a phase shift of a signal in response to various surfaces over a range of frequencies, all relative to abiotic controls. In FIG. 6, Culture 2 represents a surface having a biofilm with high biomass concentrations and Culture 11 represents a surface having a biofilm with low biomass concentrations. As depicted, the phase shift differs over the range of frequencies based at least in part on the biomass concentrations of the surface. Accordingly, phase shift can be used to measure the abundance and/or density of lipid membranes on a surface.

In alternative embodiments, changes in phase shift can further be used to determine changes in mineralogy of a surface. For instance, iron oxide reduction caused by microorganisms can be detected using phase shift at low frequencies. Phase shift can further still be used to detect microbial growth on a surface.

While the present subject matter has been described in detail with respect to specific example embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A system comprising:
a surface, wherein one or more microorganisms are present on the surface;
a flat, patterned electrode having a working electrode, a counter electrode, and a reference electrode positioned between the working electrode and the counter electrode, the flat, patterned electrode being positioned proximate the surface in non-contact relationship with the surface and the flat, patterned electrode being further positioned such that the flat, patterned electrode is not in contact with the microorganisms;
a signal source coupled to the flat, patterned electrode, the signal source configured to apply an alternating current signal to the working electrode at one or more frequencies; and
a processing device configured to detect a measured signal at the counter electrode;
wherein one or more characteristics of the measured signal at the counter electrode are indicative of one or more characteristics of the microorganisms on the surface.

2. The system of claim 1, wherein the surface is submerged in an aqueous medium.

3. The system of claim 2, wherein the sensing electrode is positioned in the aqueous medium a range of about 0.1 millimeters to about 100 centimeters above the surface.

4. The system of claim 1 wherein the one or more characteristics of microorganisms on the surface are associated with at least one of a biofilm on the surface, corrosion on the surface, or bio-corrosion on the surface.

5. The system of claim 1, wherein the measured signal at the counter electrode comprises a current signal.

6. The system of claim 1, wherein the one or more characteristics of the measured signal comprise a phase shift of the measured signal relative to the applied signal.

7. The system of claim 6, wherein the phase shift is indicative of at least one of geochemical change and microbial density.

8. The system of claim 6, wherein the one or more characteristics of the measured signal comprise one or more impedance parameters associated with a biofilm on the surface, the one or more impedance parameters determined based at least in part from the phase shift.

9. The system of claim 8, wherein the one or more impedance parameters comprise at least one of an absolute impedance, real impedance or imaginary impedance associated with the biofilm.

10. The system of claim 8, wherein at least one of the one or more impedance parameters is indicative of microbial activity associated with the surface.

11. The system of claim 1, wherein the counter electrode forms a partial arc, with at least a portion of reference and working electrodes positioned within the partial arc, and at least a portion of the counter electrode is positioned beside both the reference and working electrodes.

12. A method comprising:
positioning a flat, patterned electrode proximate a surface in non-contact relationship with the surface, wherein one or more microorganisms are present on the surface, and further positioning the flat, patterned electrode such that is not in contact with the microorganisms, the flat patterned electrode comprising a counter electrode, a working electrode, and a reference electrode positioned between the working electrode and the counter electrode;
applying an alternating current signal at the working electrode;
detecting a measured signal at the counter electrode; and
determining one or more characteristics of the measured signal;
wherein the one or more characteristics of the measured signal are indicative of one or more characteristics of the microorganisms on the surface.

13. The method of claim 12, wherein the one or more characteristics of the measured signal comprise impedance parameters associated with the surface.

14. The method of claim 13, wherein the impedance parameters comprise at least one of an absolute impedance, real impedance or imaginary impedance associated with the surface.

15. The method of claim 12, wherein the one or more characteristics of microorganisms on the surface are associated with at least one of a biofilm on the surface, corrosion on the surface, or bio-corrosion on the surface.

16. The method of claim 12, wherein the surface and the flat, patterned electrode are submerged in an aqueous medium, and the flat, patterned electrode is positioned 3 millimeters above the surface.

17. A system comprising:
a surface, wherein a biofilm is present on the surface;
a flat, patterned electrode having a working electrode, a counter electrode, and a reference electrode positioned between the working electrode and the counter electrode, the flat, patterned electrode positioned proximate the surface in non-contact relationship with the surface, wherein the flat, patterned electrode and the surface are submerged in an aqueous medium and wherein the flat, patterned electrode is further positioned such that the flat, patterned electrode is not in contact with the biofilm;
a signal source coupled to the flat, patterned electrode, the signal source configured to apply an alternating current potential at the working electrode at one or more frequencies; and
one or more processing devices configured to detect a measured alternating current at the counter electrode, the one or more processing devices further configured to determine one or more impedance parameters associated with the surface based at least in part on the applied potential and the measured current;
wherein the one or more impedance parameters are indicative of microbial activity associated with the biofilm.

18. The system of claim 17, wherein the one or more impedance parameters are determined based at least in part on a phase shift of the measured current relative to the applied potential.

19. The system of claim 18, wherein the phase shift is indicative of one or more characteristics of the biofilm on the surface.

20. The system of claim 17, wherein the microbial activity associated with the biofilm comprises microbial growth.

* * * * *